United States Patent
Freeman et al.

(10) Patent No.: US 6,796,951 B2
(45) Date of Patent: Sep. 28, 2004

(54) ANATOMICAL JOINT BRACE WITH ADJUSTABLE JOINT EXTENSION LIMITER

(75) Inventors: Brad Freeman, Mission Viejo, CA (US); James Castillo, Los Alamos, CA (US)

(73) Assignee: Asterisk.Asterisk. LLC, Foothill Ranch, CA (US)

( * ) Notice: Subject to any disclaimer, the term of this patent is extended or adjusted under 35 U.S.C. 154(b) by 378 days.

(21) Appl. No.: 09/776,523

(22) Filed: Feb. 2, 2001

(65) Prior Publication Data

US 2002/0107462 A1 Aug. 8, 2002

(51) Int. Cl.⁷ .................................................. A61F 5/00
(52) U.S. Cl. ........................................ 602/16; 602/26
(58) Field of Search .............................. 602/16, 26, 62, 602/61, 27, 23, 5

(56) References Cited

U.S. PATENT DOCUMENTS

| | | | |
|---|---|---|---|
| 1,390,915 A | | 9/1921 | Loth |
| 2,208,275 A | * | 7/1940 | McCann ..................... 623/46 |
| 2,531,486 A | | 11/1950 | Weber |
| 2,557,604 A | * | 6/1951 | Invidiato ..................... 602/16 |
| 2,558,986 A | * | 7/1951 | Seelert ..................... 602/16 |
| 2,812,961 A | * | 11/1957 | Brown et al. ................ 403/93 |
| 2,883,982 A | * | 4/1959 | Rainey ..................... 602/16 |
| 3,030,634 A | | 4/1962 | Bair |
| 3,099,448 A | | 7/1963 | Salvo et al. |
| 3,387,305 A | | 6/1968 | Shafer |
| 3,669,105 A | | 6/1972 | Castiglia |
| 3,779,654 A | | 12/1973 | Horne |
| 3,785,372 A | | 1/1974 | Craig |
| 3,817,244 A | | 6/1974 | Taylor |
| 3,900,898 A | | 8/1975 | Kerman |
| 3,901,223 A | * | 8/1975 | May ........................... 602/16 |
| 3,902,482 A | * | 9/1975 | Taylor ........................ 602/16 |
| 3,928,872 A | | 12/1975 | Johnson |
| 3,958,569 A | | 5/1976 | Vosburgh |
| 4,136,404 A | | 1/1979 | Lange |
| 4,169,467 A | | 10/1979 | Rabischong et al. |

(List continued on next page.)

FOREIGN PATENT DOCUMENTS

| | | |
|---|---|---|
| DE | 1491569 | 7/1969 |
| DE | 2432766 | 3/1975 |
| EP | 297766 A | 4/1989 |
| WO | 8404240 | 11/1984 |

*Primary Examiner*—Nicholas D. Lucchesi
*Assistant Examiner*—Huong Q. Pham
(74) *Attorney, Agent, or Firm*—Stetina Brunda Garred & Brucker (57) ABSTRACT

An anatomical brace for stabilizing and supporting a uniting pivoting joint such as a knee joint disposed between a first limb structure and a second limb structure. The brace includes first and second cuffs and a pivotable brace joint there between with two opposing pivoting assemblies. Each assembly includes forward and rearward arm members in tandem and a frame structure having a first end attached to the first cuff and a second end attached to the second cuff. Extending between the cuffs is an adjustable joint extension limiter for regulating pivotable distance of the cuffs in relation to each other. Spherical sockets movably positioned within the frame structure permit naturally-occurring multi-planar joint movement such that the brace here defined effectively limits pivotal extension distance, yet permits normal joint bendability with multi planar movability up to such limit, thereby stabilizing and supporting joint-controlled limb unions.

5 Claims, 6 Drawing Sheets

U.S. PATENT DOCUMENTS

| | | | |
|---|---|---|---|
| 4,241,730 A | | 12/1980 | Helfet |
| 4,271,831 A | | 6/1981 | Deibert |
| 4,361,142 A | * | 11/1982 | Lewis et al. .................. 602/16 |
| 4,372,298 A | | 2/1983 | Lerman |
| 4,381,768 A | | 5/1983 | Erichsen et al. |
| D269,379 S | | 6/1983 | Bledsoe |
| 4,407,276 A | | 10/1983 | Bledsoe |
| 4,428,369 A | * | 1/1984 | Peckham et al. ............. 602/16 |
| 4,433,679 A | * | 2/1984 | Mauldin et al. ............. 602/16 |
| 4,487,200 A | | 12/1984 | Feanny et al. |
| 4,489,718 A | * | 12/1984 | Martin ........................ 602/16 |
| 4,493,316 A | * | 1/1985 | Reed et al. .................. 602/16 |
| 4,494,534 A | | 1/1985 | Hutson |
| 4,503,846 A | | 3/1985 | Martin |
| 4,523,585 A | | 6/1985 | Lamb et al. |
| 4,554,913 A | | 11/1985 | Womack et al. |
| 4,556,053 A | * | 12/1985 | Irons .......................... 602/26 |
| D284,702 S | | 7/1986 | Castillo |
| 4,599,998 A | | 7/1986 | Castillo |
| 4,603,690 A | | 8/1986 | Skeen |
| 4,614,181 A | | 9/1986 | Karlsson |
| 4,620,532 A | | 11/1986 | Houswerth |
| 4,621,624 A | | 11/1986 | Rayboy |
| 4,628,916 A | | 12/1986 | Lerman et al. |
| 4,665,905 A | | 5/1987 | Brown |
| 4,681,097 A | | 7/1987 | Pansier |
| 4,697,583 A | | 10/1987 | Mason et al. |
| 4,699,129 A | | 10/1987 | Aaserude et al. |
| 4,715,363 A | | 12/1987 | Detty |
| 4,723,539 A | | 2/1988 | Townsend |
| 4,753,240 A | | 6/1988 | Sparks |
| D298,568 S | | 11/1988 | Womack |
| 4,791,916 A | | 12/1988 | Paez |
| 4,803,975 A | | 2/1989 | Meyers |
| 4,854,308 A | | 8/1989 | Drillio |
| 4,856,501 A | | 8/1989 | Castillo et al. |
| 4,886,054 A | * | 12/1989 | Castillo et al. ............... 602/26 |
| 4,928,676 A | * | 5/1990 | Pansiera ...................... 602/16 |
| 4,938,207 A | | 7/1990 | Vargo |
| 4,940,044 A | | 7/1990 | Castillo |
| 4,964,402 A | | 10/1990 | Grim et al. |
| 4,986,264 A | | 1/1991 | Miller |
| D318,736 S | | 7/1991 | Castillo |
| 5,060,640 A | * | 10/1991 | Rasmusson .................. 602/16 |
| 5,063,916 A | | 11/1991 | France et al. |
| 5,121,742 A | | 6/1992 | Engen |
| 5,135,469 A | | 8/1992 | Castillo |
| 5,230,697 A | | 7/1993 | Castillo et al. |
| 5,267,946 A | | 12/1993 | Singer et al. |
| 5,288,287 A | | 2/1994 | Castillo |
| D346,028 S | | 4/1994 | Lengyel |
| 5,302,169 A | * | 4/1994 | Taylor ........................ 602/16 |
| 5,356,370 A | * | 10/1994 | Fleming ...................... 602/16 |
| 5,395,304 A | * | 3/1995 | Tarr et al. .................... 602/26 |
| D357,070 S | | 4/1995 | Castillo |
| 5,472,412 A | * | 12/1995 | Knoth ......................... 602/26 |
| 5,547,464 A | | 8/1996 | Luttrell et al. |
| 5,571,206 A | | 11/1996 | Varn |
| 5,624,390 A | * | 4/1997 | Van Dyne .................... 602/26 |
| 5,683,353 A | * | 11/1997 | Hamersly .................... 602/16 |
| 5,800,370 A | * | 9/1998 | Kubein-Meesenburg et al. ........................... 602/26 |
| 6,001,075 A | * | 12/1999 | Clemens et al. ............. 602/16 |
| 6,464,657 B1 | * | 10/2002 | Castillo ....................... 602/26 |

* cited by examiner

ANATOMICAL JOINT BRACE WITH ADJUSTABLE JOINT EXTENSION LIMITER

CROSS REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

This invention relates in general to braces for human joint support, and in particular to an anatomical brace having cuffs situated about respective limb structures on either side of a uniting pivoting joint such as a knee joint where a pivotable brace joint connects the first and second cuffs and includes a preferably adjustable joint extension limiter for determining pivotable distance of the first and second cuff in relation to each other.

Because injury and disease can affect the health, well-being, and operability of various joints of the human body, many people prefer to protect and stabilize these joints during certain activities to thereby ward off untoward trauma. Chief among such joints that can benefit from stabilization and protection are the knee and elbow where an injury such as a sports-related abuse or impact can prevent or severely limit continued activity. One manner of protecting and stabilizing joints is to fit a wearer with an appropriate brace whereby a pivotal support member is positioned adjacent the joint and held in place usually by cuff members situated around limb structure sites above and below the supported joint. As is apparent, the cuff members are responsible for stabilizing the support member and therefore must be well secured to their associated limbs. To accomplish such securement, present cuff members are typically provided with one or more straps that are tightened around each limb structure and retained by buckles, hook-and-loop connections, or the like. Co-pending U.S. patent application Ser. No. 09/771,763, filed Jan. 29, 2001, entitled "Anatomical Brace With Rapid Release Securement Member" and incorporated herein by reference in its entirety teaches cuff members that, once adjusted for proper tightness, provide a quick-release and quick-attach mechanism for rapid as well as efficient, effective, and consistent cuff member connections. In addition to providing proper tightness and placement in a limb-surround role, each cuff member also should positively embrace the limb portions on either side of the protected joint (e.g. thigh and upper leg for knee joint). While traditional responsibility for this compressive engagement has been assigned once again to one or more straps that are tightened around each limb structure and retained by buckles or the like, co-pending U.S. patent application Ser. No. 09/578,125, filed May 24, 2000, entitled "Anatomical Joint Brace" and incorporated herein by reference in its entirety, teaches cuff members with tension-adjustable shaft members integral therewith such that torsional compression can be accomplished on embraced limb portions.

In addition to requiring proper limb structure embrace, a joint brace also requires a joint that supports, stabilizes, and protects the actual joint itself while pivotally joining the cuffs. Thus, in the knee joint for example, the joint of the brace must pivot in one bending or extension plane while also permitting multi planar motion such that the lower leg beneath the knee can be moved in a normal manner. Further, it many times is desirable to limit or regulate the distance of the pivotal extension plane at the knee while allowing normal bendability and normal multi planar motion up to the controlled extension distance. Unfortunately, however, present braces are not able to assist a user in accomplishing such an objective, thereby requiring the user to self-limit his or her movement or risk an undesirable extension. Therefore, in view of the need for extension control, a primary object of the present invention is to provide an anatomically compatible joint brace having a joint extension limiter for regulating pivotable distance of first and second limb cuffs thereof in relation to each other.

Another object of the present invention is to provide an anatomically compatible joint brace wherein the pivotal jiont extension distance can be adjusted.

Yet another object of the present invention is to provide an anatomically compatible joint brace wherein the pivotal joint extension distance is controlled by a cable assembly that includes a cable length adjuster for determining pivotable distance of the first and second cuffs in relation to each other.

These and other objects of the present invention will become apparent throughout the description thereof which now follows.

BRIEF SUMMARY OF THE INVENTION

The present invention is an anatomical brace for stabilizing and supporting a uniting pivoting joint such as a knee joint disposed between a first limb structure and a second limb structure. The brace includes a first cuff partially encompassable about the first limb structure and a second cuff partially encompassable about the second limb structure. Each cuff preferably is a generally U-shape wall structure with two arms having respective distal ends arcuately extending toward each other for juxtapositioning with respective adjacent limb structure sites. A pivotable brace joint connects the first and second cuffs and comprises two opposing pivoting assemblies each on one side of the uniting pivoting joint. Each of these assemblies includes a forward arm member and a rearward arm member which is in tandem relationship with the forward arm member, and a frame structure having a first end attached to the first cuff and a second end attached to the second cuff. Extending between the first and second cuffs is a joint extension limiter for regulating pivotable distance of the cuffs in relation to each other. Preferably, the limiter is easily adjustable at the brace site and permits full joint operation until the adjusted limit is reached. Most preferably, each assembly comprises a forward arm member having a generally perpendicularly angled first end and a generally perpendicularly angled second end, and a rearward arm member in tandem relationship with the forward arm member, and also having a generally perpendicularly angled first end and a generally perpendicularly angled second end. The assembly also includes a frame structure having a first end attached to the first cuff and a second end attached to the second cuff, and four generally spherical sockets movably positioned within the frame structure such that each spherical socket accommodates one respective perpendicular end of each respective arm member for multi-planar movement between the first and second cuffs. The joint extension limiter most preferably is a length-adjustable cable assembly providing a cable extending from the rearward arm member to the first cuff for regulating the pivotable distance.

Additional embodiments incorporating the novel joint defined herein can include an anatomical brace having cuffs with quick-connect and quick-release connectors, as well as cuffs having integral therewith at least one tensioning shaft member whereby torsional cuff tightening about the limb structure can be accomplished. By providing pivotal joints as here defined that effectively limit pivotal bend distance, yet permit normal joint bendability as well as normal multi planar movability up to such joint extension limit, the present anatomical brace allows a user to confidently and effectively stabilize and support joint-accomplished unions.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENTS

Figure 1:
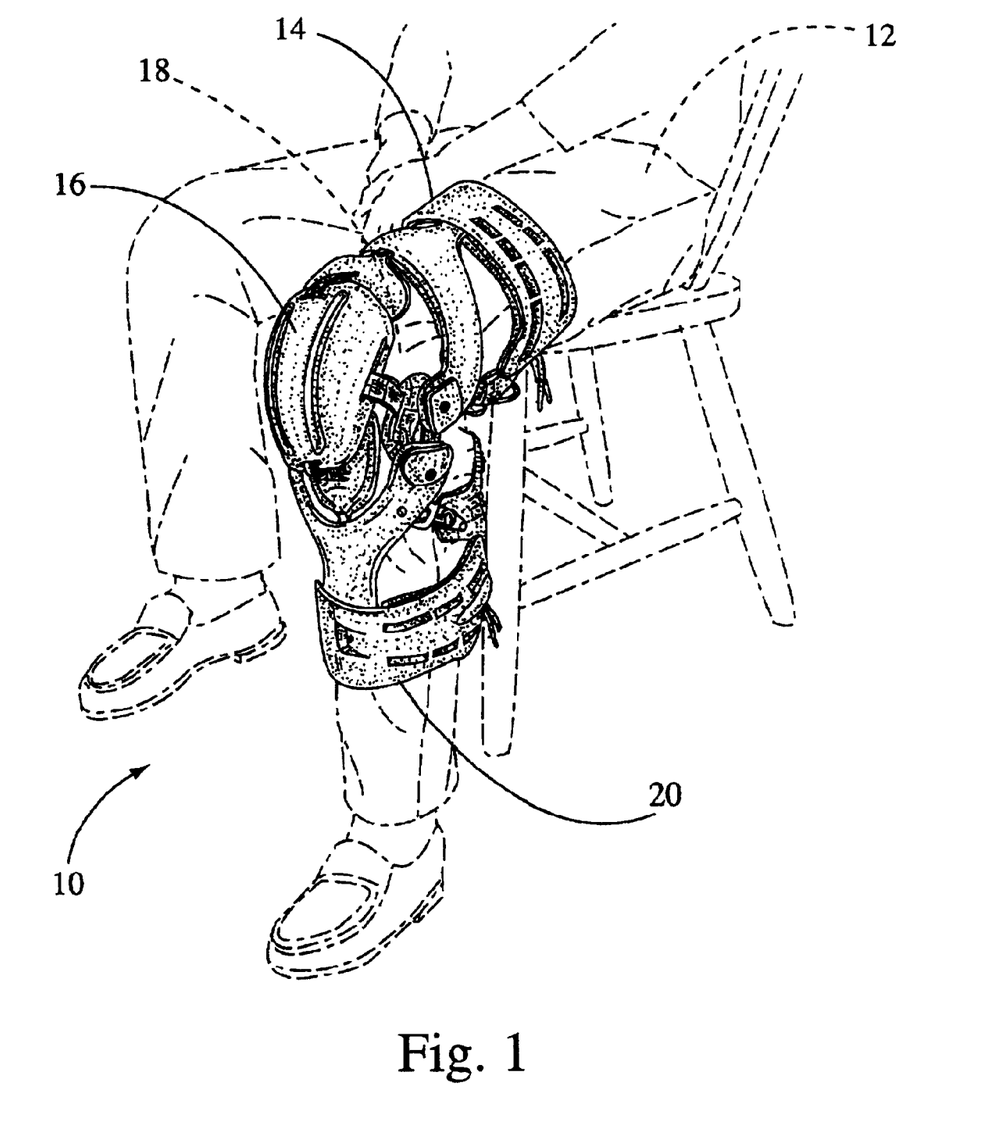
FIG. 1 is a perspective view of a knee brace with cuffs in place on a patient leg shown in phantom.
Figure 2:
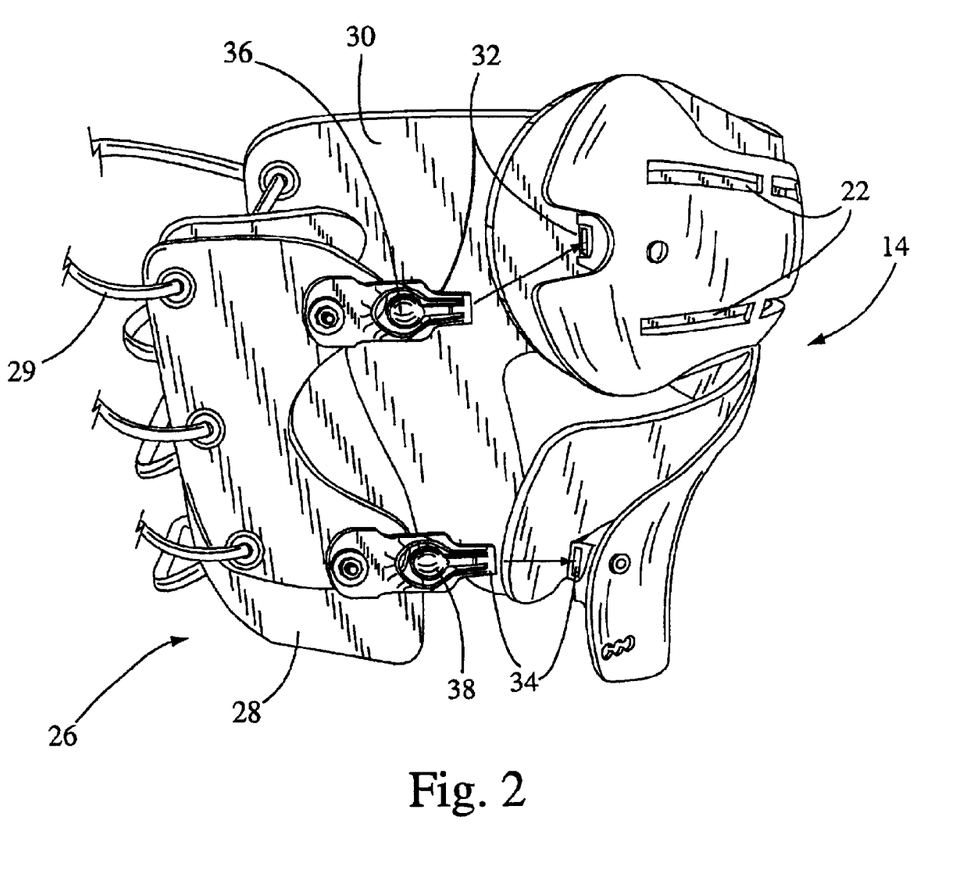
FIG. 2 is a side perspective view of the upper cuff only of FIG. 1 in disassociated relationship.
Figure 3:
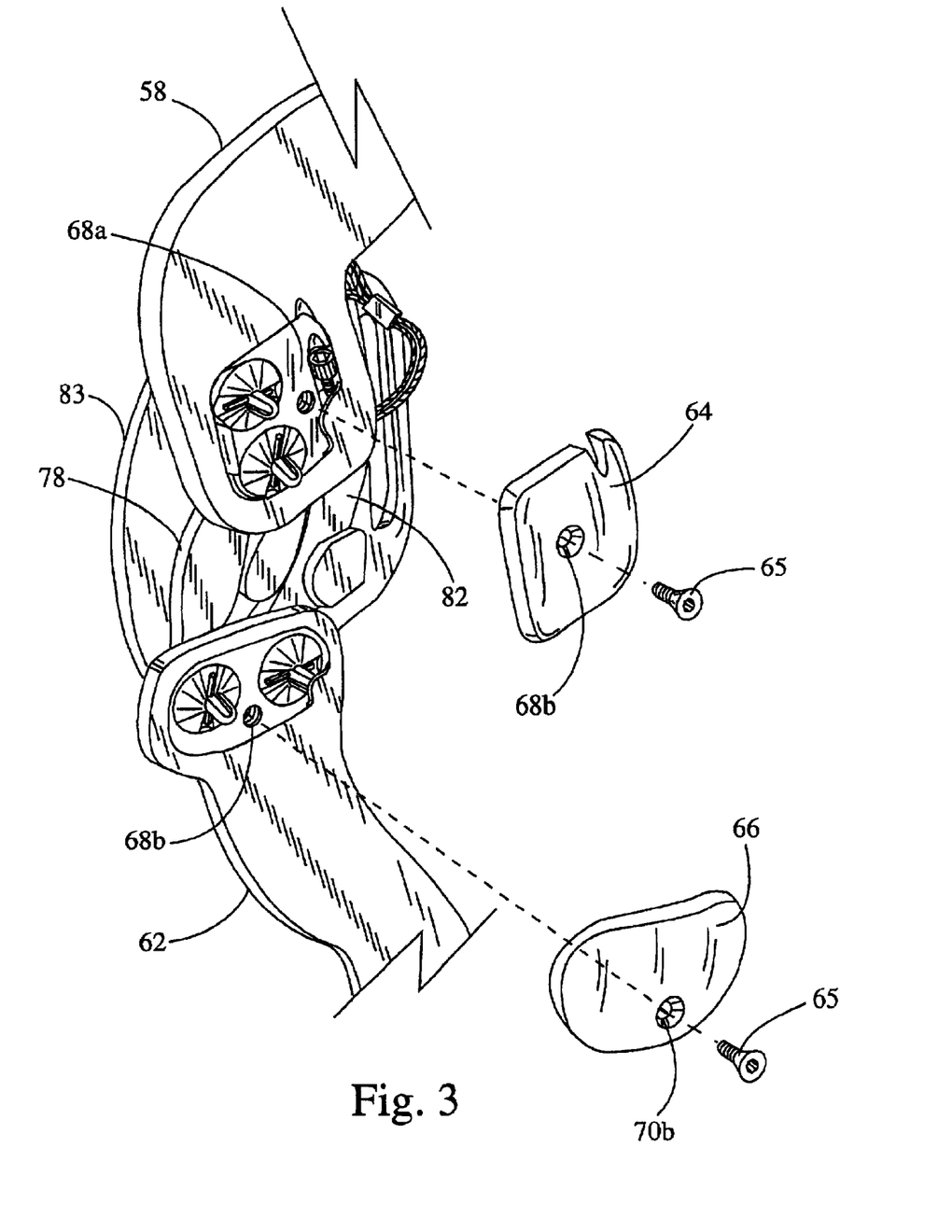
FIG. 3 is a side perspective view of the joint assembly including a portion of the brace of FIG. 1.
Figure 4:
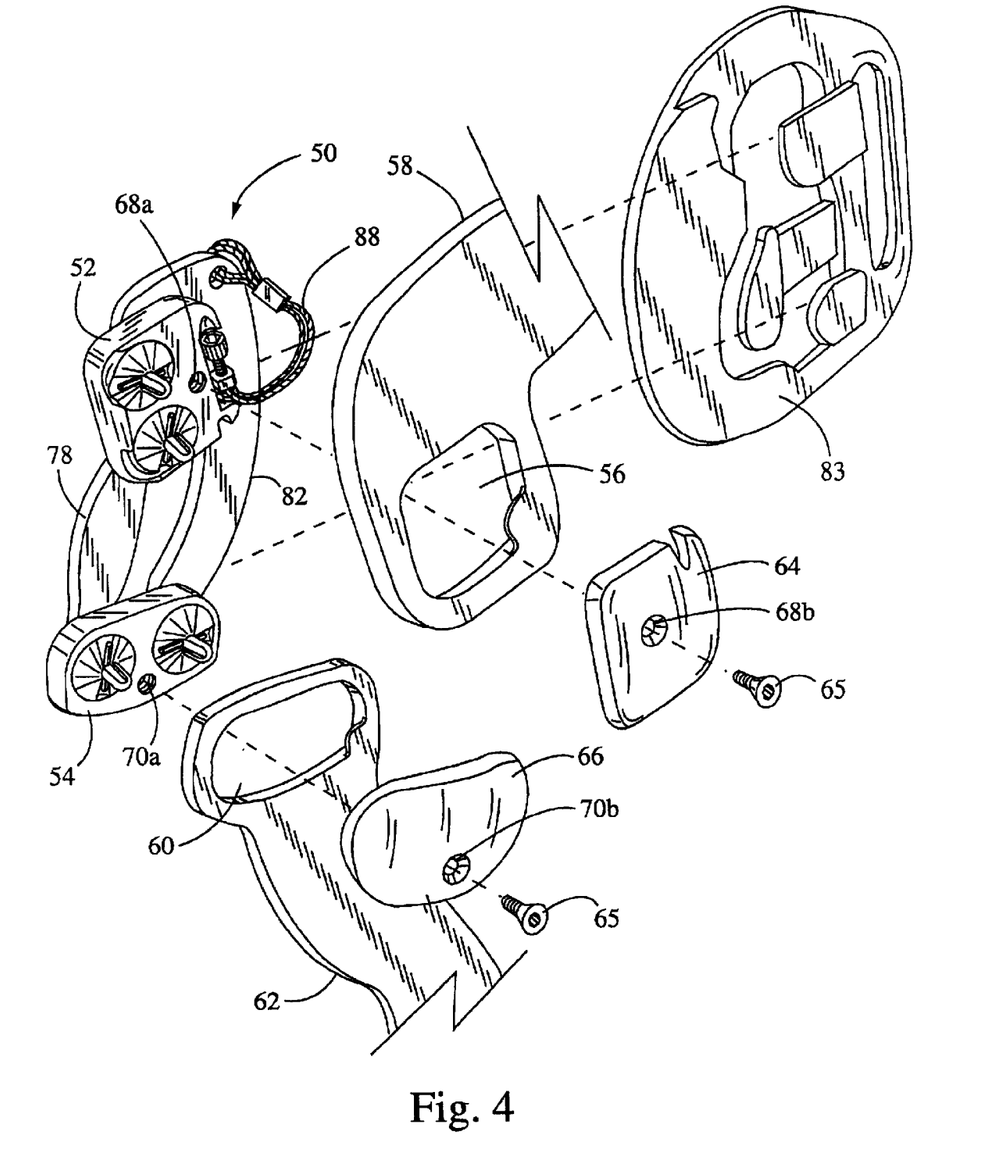
FIG. 4 is an exploded perspective view of FIG. 3.
Figures 5A, 5B:
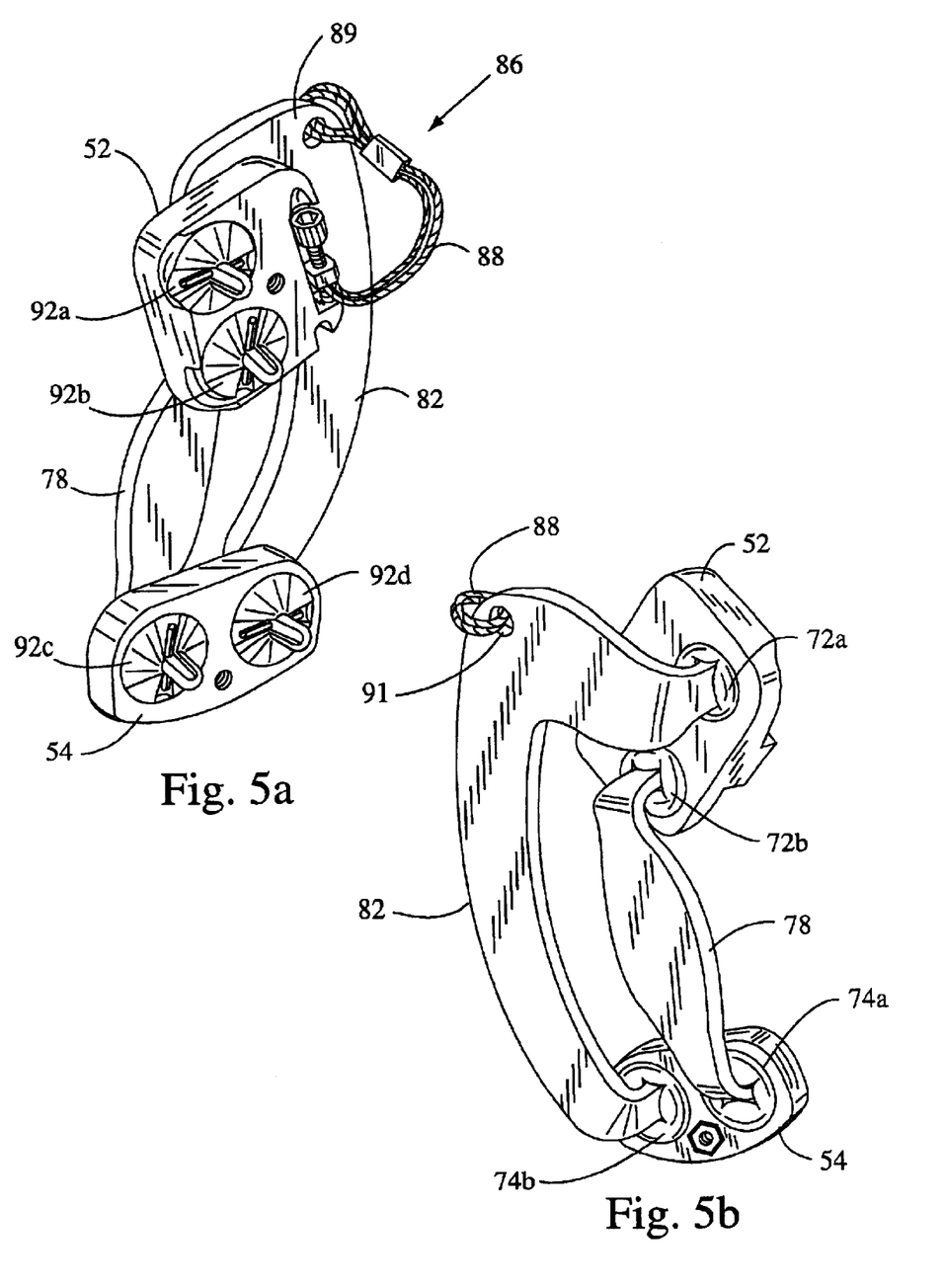
FIGS. 5a and 5b are perspective views of the front and back sides of the joint assembly of FIG. 3.
Figure 6:
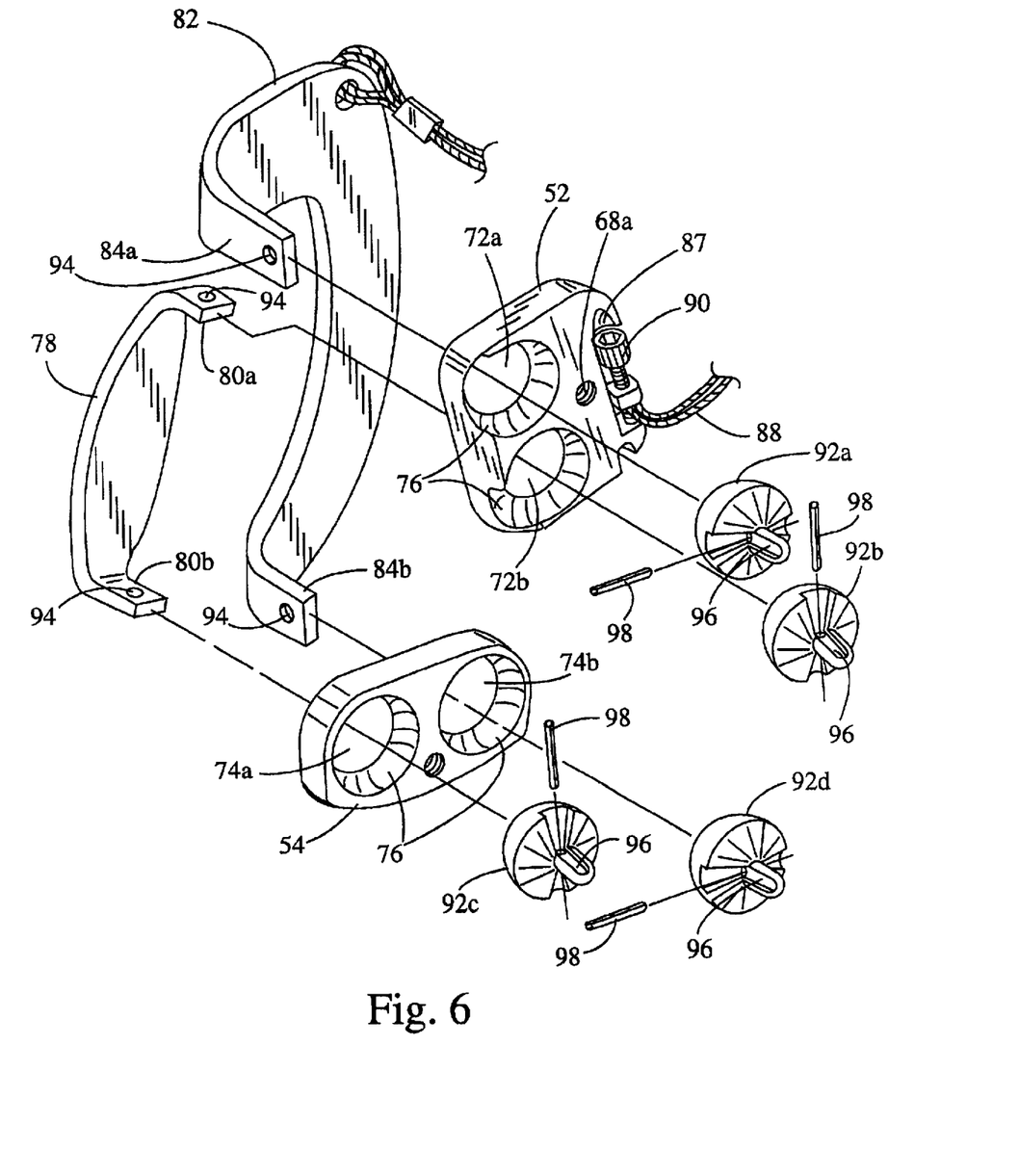
FIG. 6 is an exploded perspective view of the joint assembly of FIG. 3.

Referring first to FIGS. 1 and 2, an anatomical knee brace 10 is shown (FIG. 1) in place on a leg 12 of a human being. The brace 10 has a first cuff 14 encompassed about the limb structure above the knee joint 18 and a second cuff 20 encompassed about the limb structure below the knee joint 18. Each cuff 14, 20 is a generally U-shape, resiliently-lined wall structure, which non-limitedly can be fabricated of a polymer plastic, with the two arms of the U-shape having respective distal ends arcuately extending toward each other for juxtapositioning with respective adjacent limb structure sites. Snap-in protective patella cups 16 can be included as shown for specific impact absorption that may occur at the patella of the knee joint 18. At least one tensioning shaft member 22 is integral within each arm of each cuff 14, 20. The earlier-referenced patent application entitled "Anatomical Joint Brace" provides additional information relative cuff tensioner construction and operation. Each cuff 14, 20 has a respective cuff retainer 26 here non-limitedly exemplified as pairs of respective first and second bendable plastic limb wraps 28, 30 generally extendable toward each other from each arm for positioning around each respective limb structure and adjustably tightenable with intertwined laces 29 in substantially the same manner as a shoe is tied. At least one limb wrap 28 of a pair is attached to an arm by two releasable connectors 32, 34 having finger-operable button releases 36, 38 for disengaging the limb wrap 28 from the corresponding arm. The earlier-referenced patent application entitled "Anatomical Brace With Rapid Release Securement Member" provides additional information relative cuff retainer construction and operation.

Referring specifically to FIGS. 3–6, a pivotable brace joint pivoting assembly 50 is illustrated. The assembly 50 includes an upper housing 52 and a lower housing 54 that fit, respectively, into a complementarity shaped opening 56 of first cuff structure 58 and a complementarity shaped opening 60 of lower cuff structure 62. Once so positioned, respective caps 64, 66 are held in place with conventional set screws 65 passing respectively through apertures 68a, 68b and 70a, 70b. An interfacing plate 83 resides between the assembly 50 and the knee joint 18. Both the upper and lower housings 52, 54 have two respective openings 72a, 72b and 74a, 74b each having respective sidewalls 76 shaped to nest a spherical shape. Disposed between two openings 72b, 74a of the housings 52, 54 is a forward arm member 78 having generally perpendicularly angled first and second ends 80a, 80b directable toward the openings 72b, 74a. In like manner, a rearward arm member 82 having generally perpendicularly angled first and second ends 84a, 84b is disposed between two openings 72a, 74b of the housings 52, 54 such that the ends 84a, 84b are directable toward the openings 72a, 74b. A cable assembly 86 includes a cable 88 extending from the upper housing 52 to an upper edge portion 89 through an aperture 91 of the rearward arm member 82, and is provided with a conventional set screw 90 at one end thereof for extending or shortening the length of the cable 88 disposed between the rearward arm member 82 and upper housing 52. Such length adjustment is accomplished with an Allen wrench inserted into the enterable channel 87 leading to the set screw 90. Because the upper housing 52 resides within the structure 58 of the first cuff 14, the cable 88 functions as a joint extension limiter to determine the travel distance of the first cuff 14 from the joint and thus the pivotal distance of the first and second cuffs 14, 20 in relation to each other.

As earlier described, the sidewalls 76 of the openings 72a, 72b and 74a, 74b are shaped to nest spherical forms. As clearly illustrated in FIG. 6, spherical sockets 92a, 92b, 92c, 92d are disposed in these openings 72a, 72b and 74a, 74b in the constructed assembly 50, and each such socket accepts one respective perpendicularly angled end of forward and rearward arm members 78, 82. Each angled end 80a, 80b, 84a, 84b has an aperture 94 there through which mates with a transverse aperture 96 of each socket 92a, 92b, 92c, 92d such that respective pins 98 can pass through such mated apertures and retain the angled ends 80a, 80b, 84a, 84b within the sockets 92a, 92b, 92c, 92d. Because of the spherical interface between each socket 92a, 92b, 92c, 92d and each sidewall 76, multi planar movement of the cuffs 14, 20 in relation to each other can be accomplished. The brace joint pivoting assembly 50 thereby permits replication of normal multi planar joint movement while providing adjustable bend distances via operation of the cable assembly 86, and in this manner stabilization and support of a uniting pivoting joint disposed between a first limb structure and a second limb structure can occur.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An anatomical brace for stabilizing and supporting a uniting pivoting joint situated between a first limb structure and a second limb structure of a living being, the brace comprising:
    a) a first cuff partially encompassable about the first limb structure and a second cuff partially encompassable about the second limb structure; and
    b) a pivotable brace joint connecting the first and second cuffs, said brace joint comprising two opposing pivoting assemblies each on one side of the uniting pivoting joint, with each said assembly comprising:
        i) a forward arm member having a generally perpendicularly angled first end and a generally perpendicularly angled second end, and a rearward arm member in tandem relationship with the forward arm member, and having a generally perpendicularly angled first end and a generally perpendicularly angled second end;

ii) an upper housing attached to the first cuff and a lower housing attached to the second cuff, said upper and lower housings having four generally spherical and movably positioned sockets such that each spherical socket accommodates one respective perpendicular end of each respective arm member for multi-planar movement between said first and second cuffs; and iii) a joint extension limiter, wherein the joint extension limiter is a cable assembly comprising a cable extending from the rearward arm member to the fist cuff, the cable assembly including a cable length adjuster for determining pivotable distance of the first and second cuffs in relation to each other.

2. An anatomical brace for stabilizing and supporting a uniting pivoting joint situated between a first limb structure and a second limb structure of a living being, the brace comprising:

a) a first cuff partially encompassable about the first limb structure and a second cuff partially encompassable about the second limb structure;

b) a respective cuff retainer for securing each cuff on each respective limb, each said retainer comprising at least one externally accessible releasable connector for attaching and releasing the respective cuff to and from the respective limb structure; and c) a pivotable brace joint connecting the first and second cuffs, said brace joint comprising two opposing pivoting assemblies each on one side of the uniting pivoting joint, with each said assembly comprising:

i) a forward arm member having a generally perpendicularly angled first end and a generally perpendicularly angled second end, and a rearward arm member in tandem relationship with the forward arm member and having a generally perpendicularly angled first end and a generally perpendicularly angled second end;

ii) an upper housing attached to the first cuff and a lower housing attached to the second cuff, said upper and lower housings having four generally spherical and movably positioned sockets such that each spherical socket accommodates one respective perpendicular end of each respective arm member for multi-planar movement between said first and second cuff; and iii) a joint extension limiter, wherein the joint extension limiter is a cable assembly comprising a cable extending from the rearward arm member to the first cuff, the cable assembly including a cable length adjuster for regulating pivotable distance of the first and second cuffs in relation to each other.

3. An anatomical brace for stabilizing and supporting a uniting pivoting joint situated between a first limb structure and a second limb structure of a living being, the brace comprising:

a) a first cuff partially encompassable about the first limb structure and a second cuff partially encompassable about the second limb structure;

b) at least one tensioning shaft member integral with each cuff; and c) a pivotable brace joint connecting the first and second cuffs, said brace joint comprising two opposing pivoting assemblies each on one side of the uniting pivoting joint, with each said assembly comprising:

i) a forward arm member having a generally perpendicularly angled first end and a generally perpendicularly angled second end, and a rearward arm member in tandem relationship with the forward arm member and having a generally perpendicularly angled first end and a generally perpendicularly angled second end;

ii) an upper housing attached to the first cuff and a lower housing attached to the second cuff, said upper and lower housings having four generally spherical and movably positioned sockets such that each spherical socket accommodates one respective perpendicular end of each respective arm member for multi-planar movement between said first and second cuff; and iii) a joint extension limiter, wherein the joint extension limiter is a cable assembly comprising a cable extending from the rearward arm member to the first cuff, the cable assembly including a cable length adjuster for regulating pivotable distance of the first and second cuffs in relation to each other.

4. An anatomical brace for stabilizing and supporting a uniting pivoting joint situated between first and second limb structures of a living being, the brace comprising:

first and second cuffs encompassable about the first and second limb structures, respectively; and b) a brace joint connecting the first and second cuffs and having two opposing assemblies each on one side of the uniting pivoting joint, with each said assembly comprising:

i) forward and rearward arm members;

ii) upper and lower housings attached to the first and second cuffs, respectively; and iii) a cable assembly comprising a cable extending from the rearward arm member to the first cuff, the cable assembly including a cable length adjuster for regulating pivotable distance of the first and second cuffs in relation to each other;

wherein the upper and lower housings have four movably positioned sockets each configured to accommodate one respective perpendicular end of each respective arm member for multi-planar movement between said first and second cuff.

5. An anatomical brace as claimed in claim 4 wherein the sockets are generally spherical sockets.

* * * * *